US010048223B2

(12) United States Patent
Hisada et al.

(10) Patent No.: US 10,048,223 B2
(45) Date of Patent: Aug. 14, 2018

(54) PARTICULATE MEASUREMENT SYSTEM (71) Applicant: NGK SPARK PLUG CO., LTD., Nagoya-shi, Aichi (JP)

(72) Inventors: Kaoru Hisada, Obu (JP); Katsunori Yazawa, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 116 days.

(21) Appl. No.: 15/332,177

(22) Filed: Oct. 24, 2016

(65) Prior Publication Data

US 2017/0115251 A1    Apr. 27, 2017

(30) Foreign Application Priority Data

Oct. 27, 2015 (JP) ................... 2015-210885

(51) Int. Cl.
G01N 27/70     (2006.01)
G01N 33/00     (2006.01)

(52) U.S. Cl.
CPC ......... G01N 27/70 (2013.01); G01N 33/0011 (2013.01)

(58) Field of Classification Search
CPC ............. F02D 41/1466; G01M 15/102; G01N 15/0656; G01N 1/2252; G01N 27/70; G01N 33/0027; G01N 27/62; G01N 27/68

See application file for complete search history.

(56) References Cited

U.S. PATENT DOCUMENTS

| 3,114,877 | A | * | 12/1963 | Dunham | ................ | G01N 27/70 |
| | | | | | | 250/383 |
| 4,078,880 | A | * | 3/1978 | Hunziker | ................ | F23N 5/003 |
| | | | | | | 431/76 |
| 5,631,818 | A | * | 5/1997 | Johnson | .................... | B03C 3/66 |
| | | | | | | 363/125 |
| 6,906,322 | B2 | * | 6/2005 | Berggren | ............ | H01J 49/0454 |
| | | | | | | 250/281 |

(Continued)

FOREIGN PATENT DOCUMENTS

JP    2012047722 A  *  3/2012  ............ F01N 9/002
JP    2013-195069 A     9/2013

*Primary Examiner* — David A Rogers
(74) *Attorney, Agent, or Firm* — Sughrue Mion, PLLC (57) ABSTRACT A particulate measurement system (10) includes an auxiliary electrode current measurement circuit (780), which can determine whether or not an auxiliary electrode current $I_{ir}$ has flowed to a second wiring line (222) as well as its magnitude. When a particulate sensor (100) is operating normally, since a second electrode (132) and a casing CS are electrically insulated from each other, no current flows to the second wiring line (222). However, when the second electrode (132) and the casing CS are electrically shorted by soot or the like, the auxiliary electrode current $I_{ir}$ flows to the second wiring line (222). Therefore, by providing the auxiliary electrode current measurement circuit (780), the particulate measurement system (10) can determine the state of adhesion of particulates, etc., in the particulate sensor (100), and can determine whether or not the particulate measurement system (10) is in an anomalous state.

2 Claims, 6 Drawing Sheets (56) References Cited

U.S. PATENT DOCUMENTS

| | | | | |
|---|---|---|---|---|
| 7,406,855 | B2* | 8/2008 | Tikkanen | G01N 27/62 73/23.31 |
| 8,652,240 | B2* | 2/2014 | Sugiyama | G01N 15/0656 60/275 |
| 8,710,849 | B2* | 4/2014 | Tikkanen | G01N 1/2252 250/288 |
| 8,823,384 | B2* | 9/2014 | Matsuoka | G01N 15/0656 324/459 |
| 9,053,912 | B2* | 6/2015 | Kokubo | H01J 49/022 |
| 9,476,807 | B2* | 10/2016 | Motomura | G01N 15/0656 |
| 9,581,069 | B2* | 2/2017 | Motomura | G01N 15/0656 |
| 9,897,528 | B2* | 2/2018 | Motomura | G01N 15/0656 |
| 9,915,587 | B2* | 3/2018 | Sugiyama | G01M 15/102 |
| 2011/0050243 | A1* | 3/2011 | Tikkanen | G01N 1/2252 324/464 |
| 2012/0234172 | A1* | 9/2012 | Sugiyama | G01N 1/2252 96/26 |
| 2012/0262182 | A1* | 10/2012 | Matsuoka | G01N 15/0656 324/464 |
| 2012/0304738 | A1* | 12/2012 | Landkammer | G01N 15/0656 73/23.33 |
| 2012/0312074 | A1* | 12/2012 | Allmendinger | G01N 15/0656 73/23.31 |
| 2014/0069169 | A1* | 3/2014 | Janka | G01N 1/2252 73/28.02 |
| 2014/0352405 | A1* | 12/2014 | Motomura | G01N 15/0656 73/23.31 |
| 2015/0020574 | A1* | 1/2015 | Motomura | G01N 15/0656 73/23.31 |
| 2016/0011093 | A1* | 1/2016 | Matsuoka | G01N 15/0656 73/23.33 |

* cited by examiner

PARTICULATE MEASUREMENT SYSTEM

BACKGROUND OF THE INVENTION

1. Field of the Invention

The present invention relates to a particulate measurement system which measures the amount of particulates such as soot contained in a gas under measurement.

2. Description of the Related Art

Conventionally, a particulate measurement system has been known which measures the amount of particulates (e.g., soot) contained in a gas under measurement (for example, exhaust gas discharged from an internal combustion engine or the like) (see, for example, Patent Document 1).

Such a particulate measurement system includes a particulate sensor which is exposed to the gas under measurement and detects particulates. The particulate sensor includes an ion generation section, an electrification chamber, a trapping section, and an auxiliary electrode section.

The particulate measurement system electrifies at least a portion of particulates contained in the gas under measurement in the electrification chamber using ions generated at the ion generation section by means of corona discharge, and measures the amount of particulates based on the amount of ions trapped by the trapping section. Notably, the auxiliary electrode section is maintained at a potential which repulses the ions to thereby assist the trapping of ions at the trapping section.

Also, the particulate measurement system includes an isolation transformer for corona discharge and a corona discharge control section. The isolation transformer for corona discharge is an isolation transformer for voltage conversion of electric power used for corona discharge and includes a primary-side coil and a secondary-side coil which is connected to the ion generation section. The corona discharge control section detects a current flowing from the trapping section to a secondary-side reference potential (the reference potential of the secondary-side coil of the isolation transformer for corona discharge). Also, the corona discharge control section controls the amount of electric power supplied from the isolation transformer for corona discharge to the ion generation section based on the current such that the amount of ions generated from the ion generation section approaches a target value determined in advance.

[Patent Document 1] Japanese Patent Application Laid-Open (kokai) No. 2013-195069

3. Problems to be Solved by the Invention

However, a problem arises in the particulate measurement system described above in that when particulates (soot, etc.) adhere to the particulate sensor, the accuracy in measuring the amount of particulates is lowered or measurement of the amount of particulates can no longer be carried out.

Namely, for example, when the insulation resistance between the auxiliary electrode section and the reference potential (ground potential) decreases due to particulates, etc., having adhered to the particulate sensor, an irregular current may flow through the adhered particulates, etc. If such an irregular current flows, the measured amount of ions trapped by the trapping section is in error, which adversely affects the measurement of the amount of particulates. Also, if an irregular current is generated and the irregular current flows to a path extending from the trapping section to the secondary-side reference potential, the detected value of the current flowing from the trapping section to the secondary-side reference potential is an error. Further, the control of the amount of electric power by the corona discharge control section deviates from a normal operating state. In such a case, the amount of electric power supplied from the isolation transformer for corona discharge to the ion generation section deviates from a normal operating state and the accuracy in measuring the amount of particulates may decrease.

SUMMARY OF THE INVENTION

It is therefore an object of the present invention to provide a particulate measurement system which suppresses a decrease in measurement accuracy due to adhesion of particulates.

The above object has been achieved by providing (1) a particulate measurement system which comprises a particulate sensor for detecting particulates and a sensor drive section for driving the particulate sensor, and which measures the amount of particulates contained in a gas under measurement. The particulate sensor includes an ion generation section, an electrification chamber, a trapping section, and an auxiliary electrode section including an auxiliary electrode. The sensor drive section includes an isolation transformer for corona discharge, an isolation transformer for the auxiliary electrode, a corona discharge control section, and an auxiliary electrode current detection section.

The ion generation section generates ions by means of corona discharge. The electrification chamber is provided so as to electrify at least a portion of the particulates contained in the gas under measurement using the ions generated in the ion generation section. The trapping section traps at least a portion of the ions generated by the ion generation section but not used for electrifying the particulates. The auxiliary electrode is maintained at a potential which repulses the unused ions and which assists in the trapping of the unused ions at the trapping section.

The isolation transformer for corona discharge has a primary-side coil and a secondary-side coil and which performs voltage conversion for electric power used for generating the corona discharge. The secondary-side coil of the isolation transformer for corona discharge is connected to the ion generation section. The isolation transformer for the auxiliary electrode has a primary-side coil and a secondary-side coil, and performs voltage conversion for generating an auxiliary voltage to be applied to the auxiliary electrode, and the secondary-side coil of the isolation transformer for the auxiliary electrode is connected to the auxiliary electrode. A reference potential of the primary-side coil of the isolation transformer for corona discharge is defined as a primary-side reference potential, and a reference potential of the secondary-side coil of the isolation transformer for corona discharge is defined as a secondary-side reference potential.

The corona discharge control section detects the current flowing from the trapping section to the secondary-side reference potential and controls the amount of electric power supplied from the isolation transformer for corona discharge to the ion generation section based on the detected current such that the amount of ions generated from the ion generation section approaches a target value set in advance.

The auxiliary electrode current detection section detects an auxiliary electrode current flowing to a voltage application path for connecting the secondary-side coil of the isolation transformer for the auxiliary electrode to the auxiliary electrode section.

The secondary-side coil of the isolation transformer for the auxiliary electrode applies an auxiliary voltage to the auxiliary electrode. In a normal operating state, the secondary-side coil does not form a closed loop together with the auxiliary electrode. Thus, no current flows to the voltage application path connecting the secondary-side coil of the isolation transformer for the auxiliary electrode and the auxiliary electrode.

However, when the insulation resistance between the auxiliary electrode and the reference potential (ground potential) decreases due to, for example, particulates, etc., having adhered to the particulate sensor, an irregular current flows through the adhered particulates, etc., and a current (auxiliary electrode current) flows to the voltage application path.

Therefore, by providing the auxiliary electrode current detection section for detecting the auxiliary electrode current flowing to the voltage application path, it becomes possible to determine whether or not the auxiliary electrode current has flowed to the voltage application path. Namely, in the case where the auxiliary electrode current is detected by the auxiliary electrode current detection section, there is a possibility that an anomaly has occurred in the particulate measurement system.

Therefore, by providing the auxiliary electrode current detection section, the particulate measurement system can determine the state of adhesion of particulates, etc., in the particulate sensor, and can determine whether or not the particulate measurement system is in an anomalous state, to thereby suppress a decrease in measurement accuracy due to adhesion of particulates.

Also, the particulate measurement system can determine the state of adhesion of particulates, etc., in the particulate sensor based on the result of the detection of the auxiliary electrode current by the auxiliary electrode current detection section and can determine the timing of cleaning or exchanging the particulate sensor based on the result of the determination. Thus, it becomes possible to improve the particulate measurement accuracy.

In a preferred embodiment (2) of the above particulate measurement system (1), the corona discharge control section controls the amount of electric power supplied from the isolation transformer for corona discharge to the ion generation section based on the auxiliary electrode current, in addition to the current flowing from the trapping section to the secondary-side reference potential, such that the amount of the ions generated from the ion generation section approaches the target value set in advance.

If the auxiliary electrode current flows to the voltage application path, due to the influence of the auxiliary electrode current, the detected value of the current flowing from the trapping section to the secondary-side reference potential varies. In such a case, control of the amount of electric power by the corona discharge control section is likely to deviate from a normal operating state. As a result, the amount of electric power supplied from the isolation transformer for corona discharge to the ion generation section may deviate from the normal operating state and the accuracy in measuring the amount of particulates may decrease.

In order to overcome such a drawback, the corona discharge control section controls the amount of electric power based on the auxiliary electrode current in addition to the current flowing from the trapping section to the secondary-side reference potential. Thus, the corona discharge control section can suppress the influence of the auxiliary electrode current and prevent improper control of the amount of electric power supplied from the isolation transformer for corona discharge to the ion generation section. For example, in the case where the auxiliary electrode current flows into the path extending from the trapping section to the secondary-side reference potential, the corona discharge control section may control the amount of electric power based on a value obtained by subtracting the detected value of the auxiliary electrode current from the detected value of the current flowing from the trapping section to the secondary-side reference potential. As a result, even when the auxiliary electrode current flows, the corona discharge control section can properly control the amount of electric power supplied from the isolation transformer for corona discharge to the ion generation section, and can measure the amount of particulates while suppressing the influence of the auxiliary electrode current.

Effect of the Invention

The particulate measurement system of the present invention can suppress a decrease in measurement accuracy due to adhesion of particulates.

DESCRIPTION OF REFERENCE NUMERALS

Reference numerals used to identify various features in the drawings include the following 10 . . . particulate measurement system; 31 . . . gas flow passage; 35 . . . discharge hole; 41 . . . nozzle; 42 . . . partition wall; 45 . . . inflow hole; 55 . . . air supply hole; 100 . . . particulate sensor; 110 . . . ion generation section; 111 . . . ion generation chamber; 112 . . . first electrode; 120 . . . exhaust gas electrification section; 121 . . . electrification chamber; 130 . . . ion trapping section; 131 . . . trapping chamber; 132 . . . second electrode; 221 . . . first wiring line; 222 . . . second wiring line; 223 . . . signal line; 224 . . . air supply tube; 300 . . . sensor drive section; 440 . . . power supply section; 600 . . . sensor control section; 700 . . . electric circuit section; 710 . . . power supply circuit; 710$a$ . . . first power supply circuit; 710$b$ . . . second power supply circuit; 711$a$ . . . first discharge voltage control circuit; 711$b$ . . . second discharge voltage control circuit; 712$a$ . . . first transformer drive circuit; 712$b$ . . . second transformer drive circuit; 720 . . . isolation transformer; 720$a$ . . . first isolation transformer; 720$b$ . . . second isolation transformer; 730 . . . corona current measurement circuit; 740 . . . ion current measurement circuit; 751 . . . first rectification circuit; 752 . . . second rectification circuit; 780 . . . auxiliary electrode current measurement circuit; 800 . . . air supply section; CS . . . casing; PGL . . . primary-side ground; and SGL . . . secondary-side ground.

DETAILED DESCRIPTION OF THE PREFERRED EMBODIMENTS

The present invention will next be described in greater detail with reference to the drawings. However, the present invention should not be construed as being limited thereto.

1. First Embodiment 1-1. Overall Configuration

The configuration of a particulate measurement system according to a first embodiment will next be described.

Figure 1A:
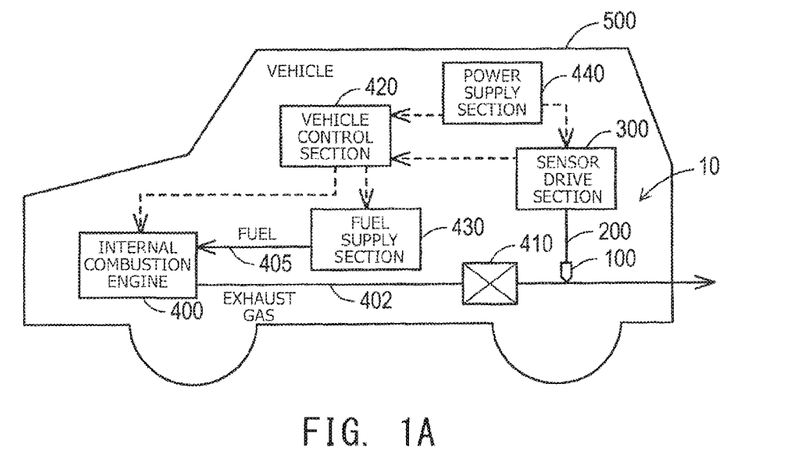
FIGS. 1A and 1B are explanatory views of an overall configuration of a particulate measurement system according to a first embodiment.
Figure 1B:
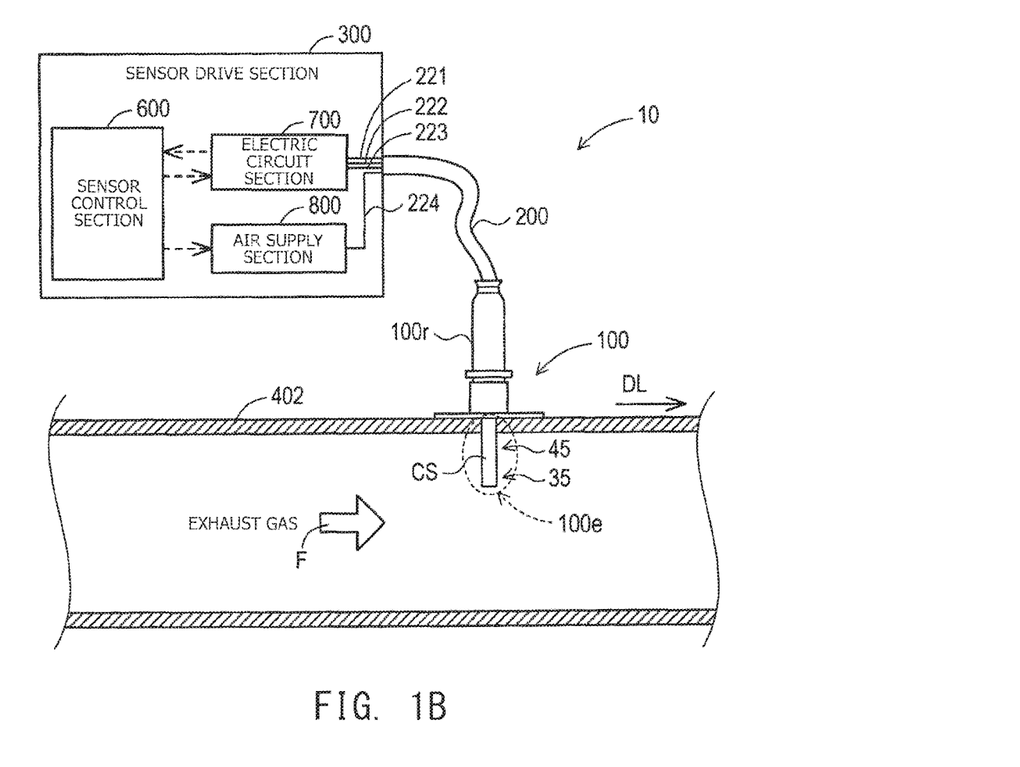

FIGS. 1A and 1B are explanatory views of an overall configuration of a particulate measurement system 10 according to the first embodiment. FIG. 1A is an explanatory view schematically exemplifying the structure of a vehicle 500 on which the particulate measurement system 10 is mounted. FIG. 1B is an explanatory view schematically exemplifying the configuration of the particulate measurement system 10 attached to the vehicle 500.

The particulate measurement system 10 includes a particulate sensor 100, a cable 200, and a sensor drive section 300, and measures the amount of particulates such as soot contained in exhaust gas discharged from an internal combustion engine 400. The internal combustion engine 400, which is a power source of the vehicle 500, is a diesel engine or the like.

The particulate sensor 100 is attached to an exhaust gas pipe 402 extending from the internal combustion engine 400, and is electrically connected to the sensor drive section 300 through the cable 200. In the present embodiment, the particulate sensor 100 is attached to a portion of the exhaust gas pipe 402, which portion is located downstream of a filter apparatus 410 (for example, a DPF (diesel particulate filter)). The particulate sensor 100 outputs to the sensor drive section 300 a signal which correlates with the amount of particulates contained in the exhaust gas.

The sensor drive section 300 drives the particulate sensor 100 and detects (measures) the amount of particulates contained in the exhaust gas based on the signal supplied from the particulate sensor 100. The "amount of particulates contained in the exhaust gas" detected by the sensor drive section 300 may be a value which is proportional to the sum of the surface areas of particulates contained in the exhaust gas or a value which is proportional to the sum of the masses of the particulates. Alternatively, the amount of particulates contained in the exhaust gas may be a value which is proportional to the number of particulates contained in a unit volume of the exhaust gas. The sensor drive section 300 is electrically connected to a vehicle control section 420 on the vehicle 500 side, and outputs to the vehicle control section 420 a signal representing the detected amount of particulates contained in the exhaust gas.

In response to the signal input from the sensor drive section 300, the vehicle control section 420 controls the combustion state of the internal combustion engine 400, the amount of fuel supplied from a fuel supply section 430 to the internal combustion engine 400 through a fuel pipe 405, etc. The vehicle control section 420 may be configured to warn a driver of the vehicle 500 about a deterioration or anomaly of the filter apparatus 410, for example, when the amount of particulates contained in the exhaust gas is greater than a predetermined amount. The sensor drive section 300 and the vehicle control section 420 are electrically connected to a power supply section 440, and electric power is supplied from the power supply section 440 to the sensor drive section 300 and the vehicle control section 420.

As shown in FIG. 1B, the particulate sensor 100 has a cylindrical distal end portion 100e, and is fixed to the outer surface of the exhaust gas pipe 402 such that the distal end portion 100e is inserted into the exhaust gas pipe 402. In the present embodiment, the distal end portion 100e of the particulate sensor 100 is inserted approximately perpendicular to an extension direction DL of the exhaust gas pipe 402. A casing CS of the distal end portion 100e has an inflow hole 45 and a discharge hole 35 formed on the surface of the casing CS. The inflow hole 45 is used to introduce the exhaust gas into the interior of the casing CS, and the discharge hole 35 is used to discharge the introduced exhaust gas to the outside of the casing CS. A portion of the exhaust gas flowing F through the exhaust gas pipe 402 is introduced into the interior of the casing CS of the distal end portion 100e through the inflow hole 45. Particulates contained in the introduced exhaust gas are electrified by ions (positive ions in the present embodiment) generated by the particulate sensor 100. The exhaust gas containing the electrified particulates is discharged to the outside of the casing CS through the discharge hole 35. The internal structure of the casing CS and the specific structure of the particulate sensor 100 will be described below.

The cable 200 is attached to a rear end portion 100r of the particulate sensor 100. The cable 200 includes a first wiring line 221, a second wiring line 222, a signal line 223, and an air supply tube 224 bundled together. Each of the wiring lines 221 to 223 and the air supply tube 224, which constitute the cable 200, is formed of a flexible member. The first wiring line 221, the second wiring line 222, and the signal line 223 are electrically connected to an electric circuit section 700 of the sensor drive section 300, and the air supply tube 224 is connected to an air supply section 800 of the sensor drive section 300.

The sensor drive section 300 includes a sensor control section 600, the electric circuit section 700, and the air supply section 800. The sensor control section 600 and the electric circuit section 700 are electrically connected to each other, and the sensor control section 600 and the air supply section 800 are electrically connected to each other.

The sensor control section 600 includes a microcomputer, and controls the electric circuit section 700 and the air supply section 800. Also, the sensor control section 600 detects (measures) the amount of particulates contained in the exhaust gas from a signal supplied from the electric circuit section 700, and outputs to the vehicle control section 420 a signal representing the amount of particulates contained in the exhaust gas.

The electric circuit section 700 supplies electric power to the particulate sensor 100 through the first wiring line 221 and the second wiring line 222 so as to drive the particulate sensor 100. A signal which correlates with the amount of particulates contained in the exhaust gas is supplied from the particulate sensor 100 to the electric circuit section 700 through the signal line 223. Using the signal supplied through the signal line 223, the electric circuit section 700 outputs to the sensor control section 600 a signal corresponding to the amount of particulates contained in the exhaust gas. These signals will be described in detail below.

The air supply section 800 includes a pump (not shown), and supplies high-pressure air to the particulate sensor 100 through the air supply tube 224 in response to an instruction from the sensor control section 600. The high-pressure air supplied from the air supply section 800 is used to drive the particulate sensor 100. Notably, instead of supplying air from the air supply section 800, another type of gas may be supplied to the particulate sensor 100.

1-2. Particulate Sensor

Figure 2:
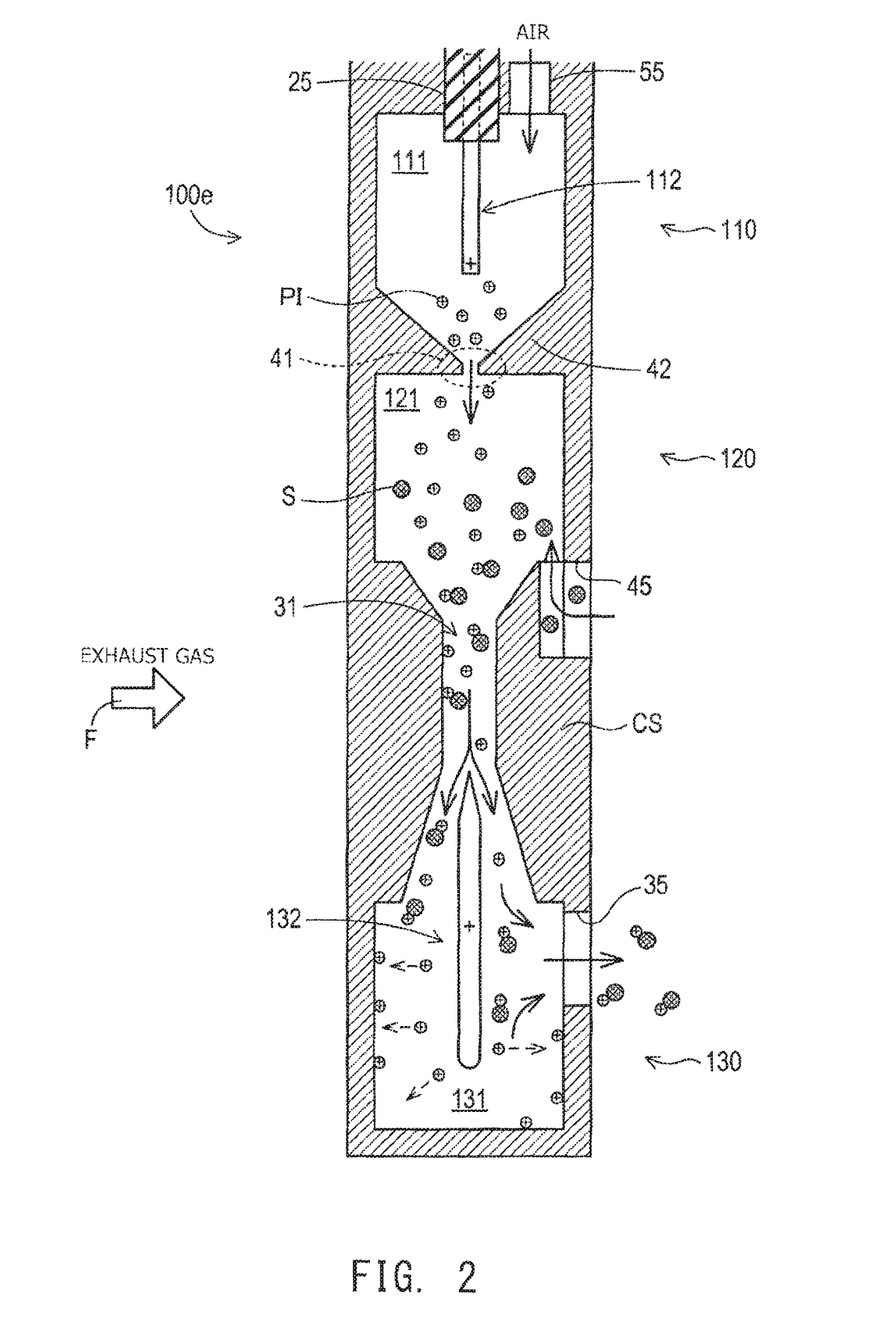
FIG. 2 is an explanatory view schematically showing the structure of a distal end portion of a particulate sensor.

FIG. 2 is an explanatory view schematically showing the structure of the distal end portion 100e of the particulate sensor 100.

The distal end portion 100e of the particulate sensor 100 includes an ion generation section 110, an exhaust gas electrification section 120, and an ion trapping section 130. The casing CS has a structure in which the three mechanism sections; i.e., the ion generation section 110, the exhaust gas electrification section 120, and the ion trapping section 130, are arranged in this order from the proximal end side (the upper side in FIG. 2) of the distal end portion 100e toward the distal end side (the lower side in FIG. 2) thereof (along the axial direction of the particulate sensor 100). The casing CS is formed of an electrically conductive material, and is connected to a secondary-side ground SGL (FIG. 3) through the signal line 223 (FIG. 1B).

The ion generation section 110 is a mechanism which generates ions (positive ions in the present embodiment) which are supplied to the exhaust gas electrification section 120. The ion generation section 110 includes an ion generation chamber 111 and a first electrode 112. The ion generation chamber 111 is a small space formed inside the casing CS. An air supply hole 55 and a nozzle 41 are provided on the inner circumferential surface of the ion generation chamber 111. The first electrode 112 is attached such that it projects into the ion generation chamber 111. The air supply hole 55 communicates with the air supply tube 224 (FIG. 1B), and high-pressure air supplied from the air supply section 800 (FIG. 1B) is supplied to the ion generation chamber 111 through the air supply hole 55. The nozzle 41 is a very small hole (orifice) provided near the center of a partition wall 42 provided between the ion generation section 110 and the exhaust gas electrification section 120. The nozzle 41 supplies the ions generated in the ion generation chamber 111 to an electrification chamber 121 of the exhaust gas electrification section 120. The first electrode 112 has a rod-like outer shape, and its base end portion is fixed to the casing CS via a ceramic pipe 25 in a state in which a distal end portion of the first electrode 112 is located near the partition wall 42. The first electrode 112 is connected to the electric circuit section 700 (FIG. 1B) through the first wiring line 221 (FIG. 1B).

The ion generation section 110 is configured such that, using the electric power supplied from the electric circuit section 700, a voltage (e.g., 2 to 3 kV) is applied between the first electrode 112 (positive pole) and the partition wall 42 (negative pole). As a result, the ion generation section 110 produces a corona discharge between a distal end portion of the first electrode 112 and the partition wall 42 to thereby generate positive ions PI. The positive ions PI generated in the ion generation section 110 are jetted into the electrification chamber 121 of the exhaust gas electrification section 120 through the nozzle 41 together with the high-pressure air supplied from the air supply section 800 (FIG. 1B). The jetting speed of air jetted from the nozzle 41 may be set to a speed near the speed of sound.

The exhaust gas electrification section 120 electrifies the particulates contained in the exhaust gas by positive ions PI, and includes the above-mentioned electrification chamber 121. The electrification chamber 121 is a small space located adjacent to the ion generation chamber 111, and communicates with the ion generation chamber 111 through the nozzle 41. Also, the electrification chamber 121 communicates with the outside of the casing CS through the inflow hole 45, and communicates with a trapping chamber 131 of the ion trapping section 130 through a gas flow passage 31.

The electrification chamber 121 is configured such that, when air containing the positive ions PI are jetted from the nozzle 41, a negative pressure is created in the electrification chamber 121, and the exhaust gas located outside the casing CS flows into the electrification chamber 121 through the inflow hole 45. Therefore, the air jetted from the nozzle 41 and containing the positive ions PI and the exhaust gas flowing inward through the inflow hole 45 are mixed together within the electrification chamber 121. At that time, at least a portion of the soot S (particulates) contained in the exhaust gas that has flowed inward through the inflow hole 45 is electrified by the positive ions PI supplied from the nozzle 41. The air containing the electrified soot S and the unused positive ions PI is supplied to the trapping chamber 131 of the ion trapping section 130 through the gas flow passage 31.

The ion trapping section 130 traps ions not used for electrifying the soot S (particulates), and includes the above-mentioned trapping chamber 131 and a second electrode 132. The trapping chamber 131 is a small space located adjacent to the electrification chamber 121, and communicates with the electrification chamber 121 through the gas flow passage 31. Also, the trapping chamber 131 communicates with the outside of the casing CS through the discharge hole 35. The second electrode 132 has a generally rod-like outer shape and is fixed to the casing CS such that its longitudinal direction coincides with the flow direction of air flowing through the gas flow passage 31 (the extending direction of the casing CS). The second electrode 132 is connected to the electric circuit section 700 (FIG. 1B) through the second wiring line 222 (FIG. 1B). The second electrode 132 is electrically insulated from the casing CS.

A voltage of about 100 V is applied to the second electrode 132, whereby it functions as an auxiliary electrode for trapping positive ions not used for electrifying the soot S. Specifically, using the electric power supplied from the electric circuit section 700, a voltage is applied to the ion trapping section 130 such that the second electrode 132 serves as a positive pole, and the casing CS constituting the electrification chamber 121 and the trapping chamber 131 serves as a negative pole. As a result, the positive ions PI not used for electrifying the soot S are repulsed by the second electrode 132, whereby the advancing directions of the positive ions PI deviate to directions away from the second electrode 132. The deviated positive ions PI are trapped by the inner circumferential walls of the trapping chamber 131 and the gas flow passage 31 which function as a negative pole. Meanwhile, the soot S to which positive ions PI have adhered are also repulsed by the second electrode 132 as in the case of the positive ions PI. However, since the soot S particulates are larger in mass than the positive ions PI, the influence of the repulsive force on the advancing directions of the electrified soot S is small as compared with the case of the positive ions PI. Therefore, the electrified soot S are discharged to the outside of the casing CS through the discharge hole 35 as a result of the flow of the exhaust gas.

The particulate sensor 100 outputs a signal indicating a change in current which corresponds to the amount of positive ions PI trapped in the ion trapping section 130. The sensor control section 600 (FIG. 1B) detects the amount of soot S contained in the exhaust gas based on the signal output from the particulate sensor 100. A method of calculating the amount of soot S contained in the exhaust gas from the signal output from the particulate sensor 100 will be described below.

1-3. Electric Circuit Section

Figure 3:
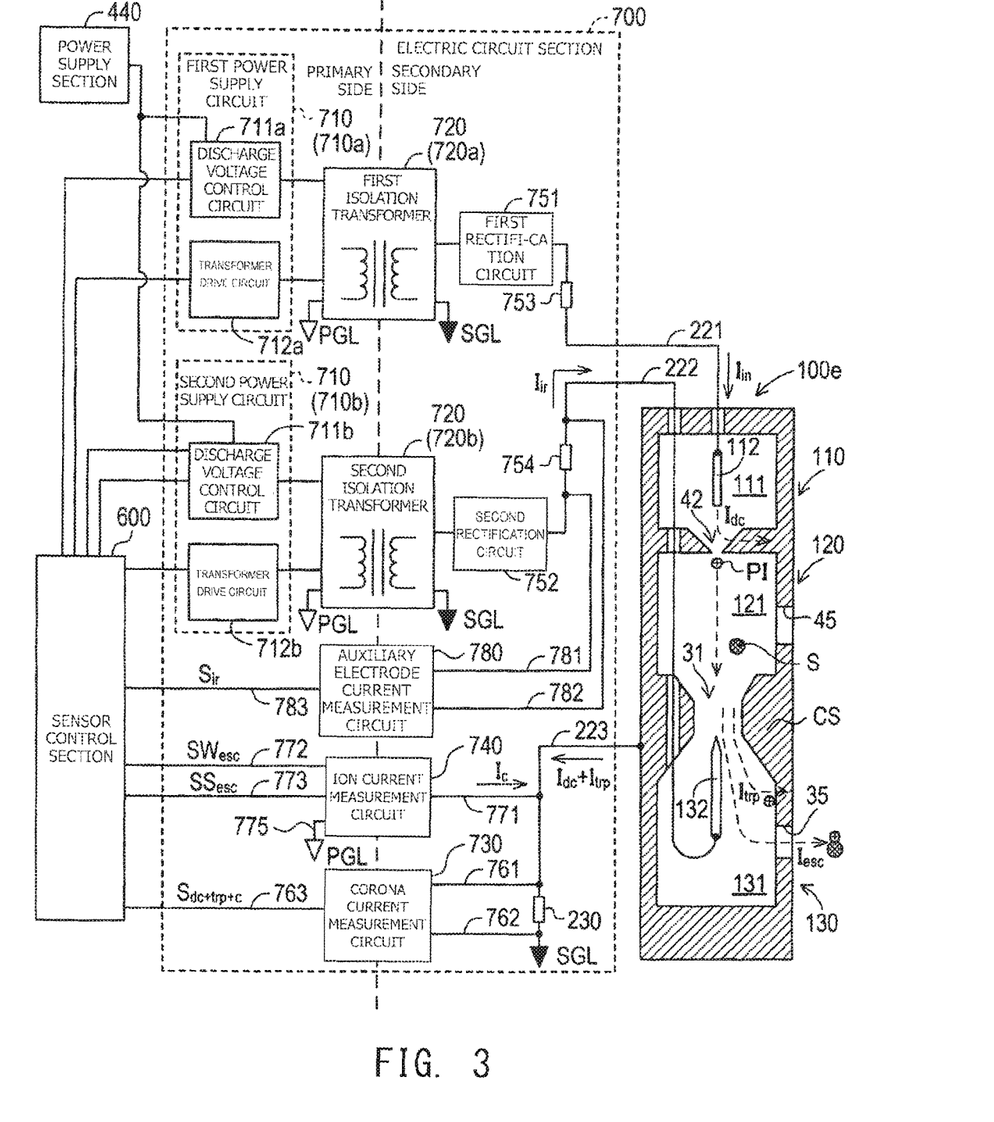
FIG. 3 is a block diagram schematically exemplifying the configuration of an electric circuit section.

FIG. 3 is a block diagram schematically exemplifying the configuration of the electric circuit section 700.

The electric circuit section 700 includes a power supply circuit 710, an isolation transformer 720, a corona current measurement circuit 730, an ion current measurement circuit 740, a first rectification circuit 751, a second rectification circuit 752, and an auxiliary electrode current measurement circuit 780.

The power supply circuit 710 includes a first power supply circuit 710a and a second power supply circuit 710b. The isolation transformer 720 includes a first isolation transformer 720a and a second isolation transformer 720b.

The first power supply circuit 710a steps up the voltage (electric power) supplied from the power supply section 440, supplies the stepped up voltage to the first isolation transformer 720a, and drives the first isolation transformer 720a. The first power supply circuit 710a includes a first discharge voltage control circuit 711a and a first transformer drive circuit 712a. Under the control by the sensor control section 600, the first discharge voltage control circuit 711a can arbitrarily change the voltage of the electric power supplied to the first isolation transformer 720a. In the present embodiment, the sensor control section 600 controls the voltage of the electric power supplied to the first isolation transformer 720a such that an input current $I_{in}$ supplied to the first electrode 112 of the particulate sensor 100 through the first wiring line 221 becomes equal to a target current $I_{ta}$ (e.g., 5 μA) set in advance. The method of this control will be described below. As a result, the amount of positive ions PI generated by the corona discharge in the ion generation section 110 can be made constant.

The first transformer drive circuit 712a includes a switch which can switch the flow direction of current flowing through the primary-side coil of the first isolation transformer 720a. The first transformer drive circuit 712a drives the first isolation transformer 720a by the switching operation of the switch. In the present embodiment, the circuit type of the first isolation transformer 720a is a push-pull type. However, the circuit type of the first isolation transformer 720a is not limited thereto and may be, for example, a half-bridge type or a full-bridge type.

The first isolation transformer 720a performs voltage conversion for the electric power supplied from the first power supply circuit 710a, and supplies the voltage-converted electric power to the first rectification circuit 751 on the secondary side. The first isolation transformer 720a of the present embodiment is configured such that the primary-side coil and the secondary-side coil are not in physical contact with each other but are magnetically coupled with each other. A circuit on the primary side of the first isolation transformer 720a includes the sensor control section 600 and the power supply section 440 as well as the first power supply circuit 710a. A circuit on the secondary side of the first isolation transformer 720a includes the particulate sensor 100 and the first rectification circuit 751.

The second power supply circuit 710b steps up the voltage of electric power (DC electric power in the present embodiment) supplied from the power supply section 440, supplies the stepped up voltage to the second isolation transformer 720b, and drives the second isolation transformer 720b. The second power supply circuit 710b includes a second discharge voltage control circuit 711b and a second transformer drive circuit 712b. Under the control by the sensor control section 600, the second discharge voltage control circuit 711b can arbitrarily change the voltage of the electric power supplied to the second isolation transformer 720b. In the present embodiment, the sensor control section 600 controls the voltage of the electric power supplied to the second isolation transformer 720b such that the voltage supplied to the second electrode 132 of the particulate sensor 100 through the second wiring line 222 becomes equal to a target voltage (e.g., 100 V) set in advance.

The second transformer drive circuit 712b includes a switch which can switch the flow direction of current flowing through the primary-side coil of the second isolation transformer 720b. The second transformer drive circuit 712b drives the second isolation transformer 720b by the switching operation of the switch. In the present embodiment, the circuit type of the second isolation transformer 720b is a push-pull type. However, the circuit type of the second isolation transformer 720b is not limited thereto and may be, for example, a half-bridge type or a full-bridge type.

The second isolation transformer 720b performs voltage conversion for the electric power supplied from the second power supply circuit 710b, and supplies the voltage-converted electric power to the second rectification circuit 752 on the secondary side. The second isolation transformer 720b of the present embodiment is configured such that the primary-side coil and the secondary-side coil are not in physical contact with each other but are magnetically coupled with each other. A circuit on the primary side of the second isolation transformer 720b includes the sensor control section 600 and the power supply section 440 as well as the second power supply circuit 710b. A circuit on the secondary side of the second isolation transformer 720b includes the particulate sensor 100 and the second rectification circuit 752.

The corona current measurement circuit 730, the ion current measurement circuit 740, and the auxiliary electrode current measurement circuit 780 are provided between the circuit on the primary side of the isolation transformer 720 (the first isolation transformer 720a and the second isolation transformer 720b) and the circuit on the secondary side of the isolation transformer 720 (the first isolation transformer 720a and the second isolation transformer 720b), and are electrically connected to the primary-side and secondary-side circuits, respectively. As described below, the corona current measurement circuit 730 is configured such that a circuit portion electrically connected to the circuit on the primary side of the isolation transformer 720 (the first isolation transformer 720a and the second isolation transformer 720b) is physically insulated from a circuit portion electrically connected to the circuit on the secondary side of the isolation transformer 720 (the first isolation transformer 720a and the second isolation transformer 720b). Here, a ground (ground wiring) which has the reference potential of the primary-side circuit is also referred to as a "primary-side ground PGL," and a ground which has the reference potential of the secondary-side circuit is also referred to as a "secondary-side ground SGL."

Ends of the primary-side coils of the isolation transformer 720 (the first isolation transformer 720a and the second isolation transformer 720b) are connected to the primary-side ground PGL, and ends of the secondary-side coils thereof are connected to the secondary-side ground SGL. One end of the signal line 223 is connected to the casing CS, and the other end of the signal line 223 is connected to the secondary-side ground SGL.

The first rectification circuit 751 is connected to the first electrode 112 through a short protection resistor 753, and supplies the converted electric power to the first electrode 112 through the first wiring line 221. Namely, the voltage supplied from the first rectification circuit 751 becomes mostly a discharge voltage at the first electrode 112, and the current supplied from the first rectification circuit 751 becomes an input current $I_{in}$ input to the first electrode 112. The second rectification circuit 752 is connected to the second electrode 132 through a short protection resistor 754, and applies the converted voltage to the second electrode 132 through the second wiring line 222.

The ion current measurement circuit 740 detects a current ($I_{ese}$) corresponding to the positive ions PI having flowed out without being trapped by the ion trapping section 130 and supplies to the secondary-side circuit a current (compensation current $I_c$) corresponding to the positive ions PI having flowed out. The ion current measurement circuit 740 is connected to the signal line 223 on the secondary side (specifically, a portion of the signal line 223 located between the casing CS and the shunt resistor 230) through a wiring line 771, and is connected to the sensor control section 600 on the primary side through wiring lines 772 and 773. Also, the ion current measurement circuit 740 is connected to the primary-side ground PGL through the wiring line 775. Through the wiring line 772, the ion current measurement circuit 740 outputs to the sensor control section 600 a signal $SW_{esc}$ showing a current corresponding to the amount of positive ions PI having flowed out without having been trapped by the ion trapping section 130. The ion current measurement circuit 740 also outputs a signal $SS_{esc}$, to the sensor control section 600 through the wiring line 773, the signal $SS_{esc}$ being obtained by amplifying the signal $SW_{esc}$ and serving as a high sensitivity signal.

The corona current measurement circuit 730 is connected to the signal line 223 through wiring lines 761 and 762, and is connected to the sensor control section 600 through a wiring line 763. The wiring lines 761 and 762 are connected to the signal line 223 such that the shunt resistor 230 provided in the signal line 223 is located between the wiring lines 761 and 762. The corona current measurement circuit 730 outputs to the sensor control section 600 a signal $S_{dc-trp-c}$ representing a secondary-side current ($I_{dc}+I_{trp}+I_c$) flowing from the casing CS toward the secondary-side ground SGL through the signal line 223. Here, a "signal representing a current" is not limited to a signal which directly represents the current, and may be a signal which indirectly represents the current. For example, the "signal representing a current" may be a signal on the basis of which the current can be specified by applying a computation expression or a map to information obtained from the signal. Notably, since the compensation current $I_c$ supplied (supplemented) from the ion current measurement circuit 740 corresponds to the current corresponding to the positive ions PI having flowed out of the casing CS, the secondary-side current which includes the compensation current $I_c$ and which flows from the casing CS to the secondary-side ground SGL; i.e., the secondary-side current ($I_{dc}+I_{trp}+I_c$) flowing through the shunt resistor 230, becomes equal to the input current $I_{in}$.

Using the signal $S_{dc+trp+c}$ supplied from the corona current measurement circuit 730, the sensor control section 600 controls the first discharge voltage control circuit 711a such that the input current $I_{in}$ becomes equal to the target current $I_{ta}$. Namely, the corona current measurement circuit 730 and the sensor control section 600 constitute a constant current circuit for maintaining the corona current (=the input current $I_{in}$) at a constant level. Since the corona current correlates with the amount of positive ions PI generated at the ion generation section 110, the amount of positive ions PI generated at the ion generation section 110 is maintained constant by this constant current circuit.

Next, a method will be described by which the ion current measurement circuit 740 detects the current corresponding to the positive ions PI having flowed out without having been trapped by the ion trapping section 130.

Here, the current supplied from the first wiring line 221 to the first electrode 112 is referred to as the "input current Iin"; the current flowing from the first electrode 112 to the casing CS through the partition wall 42 due to corona discharge is referred to as the "discharge current $I_{dc}$"; the current corresponding to the charge of the positive ions PI which are some of the positive ions PI generated due to corona discharge, are used for electrification of the soot S, and leak to the outside of the casing CS will be referred to as the "leakage current $I_{esc}$"; and the current corresponding to the charge of the positive ions PI trapped by the casing CS is referred to as the "trapped current $I_{trp}$." These four currents satisfy the relation of expression (1) shown in the following [F1].

[F1]

$$I_{in}=I_{dc}+I_{trp}+I_{esc} \quad (1)$$

In expression (1), the leakage current $I_{esc}$ is a signal which is output from the ion current measurement circuit 740 and which represents a current value corresponding to the current (the compensation current $I_c$) corresponding to the positive ions PI that have flowed out. Therefore, by detecting this compensation current $I_c$, the ion current measurement circuit 740 can detect the current ($I_{esp}$) corresponding to the positive ions PI having flowed out without having been trapped by the ion trapping section 130. Notably, the compensation current $I_c$ is also a signal representing the difference between the primary-side ground PGL and the secondary-side ground PGL.

The auxiliary electrode current measurement circuit 780 is connected to the second wiring line 222 through wiring lines 781 and 782, and is connected to the sensor control section 600 through a wiring line 783. The wiring line 781 and the wiring line 782 are connected to the second wiring line 222 such that the short protection resistor 754 provided in the second wiring line 222 is located between the wiring lines 781 and 782. The short protection resistor 754 functions as a resistor for short circuit protection when a short circuit is formed, and also functions as a shunt resistor for current detection.

The auxiliary electrode current measurement circuit 780 outputs to the sensor control section 600 an auxiliary electrode current signal $S_{ir}$ representing the auxiliary electrode current $I_{ir}$ flowing to the second wiring line 222. When the particulate sensor 100 is operating normally, no current flows to the second wiring line 222 because the second electrode 132 and the casing CS are electrically insulated from each other. However, for example, when the second electrode 132 and the casing CS are electrically connected to each other (i.e., a short circuit is formed therebetween) by soot or the like, the auxiliary electrode current $I_{ir}$ may flow to the second wiring line 222. Here, a "signal representing a current" is not limited to a signal which directly represents the current, and may be a signal which indirectly represents the current. For example, the "signal representing a current" may be a signal wherein the current is specified by applying a computation expression or a map to information obtained from the signal.

1-4. Ion Current Measurement System

Figure 4:
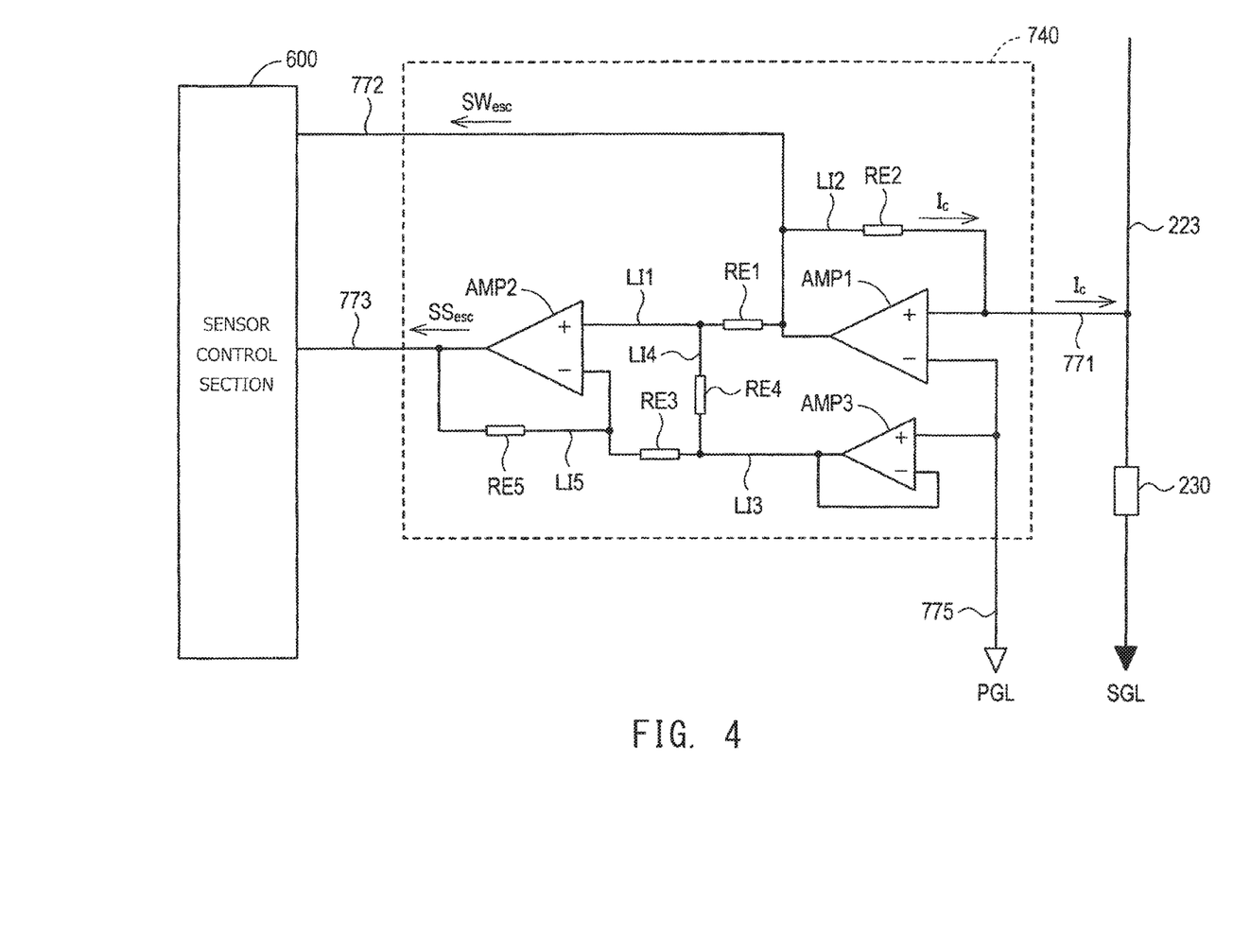
FIG. 4 is a circuit diagram schematically exemplifying the configuration of an ion current measurement circuit.

FIG. 4 is an explanatory view schematically exemplifying the configuration of the ion current measurement circuit 740.

The ion current measurement circuit 740 includes a first operational amplifier AMP1, a second operational amplifier AMP2, a third operational amplifier AMPS, and resistors RE1 to RE5 having known resistances.

One input terminal of the first operational amplifier AMP1 is connected to the secondary-side ground SGL through the wiring line 771 and the signal line 223 (including the shunt resistor 230), and the other input terminal of the first operational amplifier AMP1 is connected to the primary-side ground PGL through the wiring line 775. The output terminal of the first operational amplifier AMP1 is connected to the sensor control section 600 through the wiring line 772. Also, the output terminal of the first operational amplifier AMP1 is connected to one input terminal of the second operational amplifier AMP2 through a portion of the wiring line 772 and a wiring line LI1, and is connect to the wiring line 771 through a portion of the wiring line 772 and a wiring line LI2. The resistor RE1 is provided in the wiring line LI1, and the resistor RE2 is provided in the wiring line LI2.

One input terminal of the second operational amplifier AMP2 is connected to the first operational amplifier AMP1 through a portion of the wiring line LH and the wiring line 772, and the other input terminal of the second operational amplifier AMP2 is connected to the primary-side ground PGL through a wiring line LI3 and the wiring line 775. The resistor RE3 and the third operational amplifier AMP3 are provided in the wiring line LI3. A wiring line LI4 is connected to the wiring line LI3 at a position between the resistor RE3 and the third operational amplifier AMP3. The wiring line LI3 is connected to the wiring line LH through the wiring line LI4 in which the resistor RE4 is provided. The third operational amplifier AMP3 forms a voltage follower which suppresses voltage change due to current change on the output side. The output terminal of the second operational amplifier AMP2 is connected to the sensor control section 600 through the wiring line 773, and is connected to the wiring line LI3 through the wiring line 773 and a wiring line LI5. The resistor RE5 is provided in the wiring line LI5.

When the leakage current $I_{esc}$ is generated, the reference potential of the secondary-side ground SGL becomes lower than the reference potential of the primary-side ground PGL in accordance with the magnitude of the leakage current $I_{esc}$. This is because a difference in energy corresponding to the leakage current $I_{esc}$ is produced between the energy (electric power) supplied from the primary-side circuit (including the power supply circuit 710) to the particulate sensor 100 and the energy (electric power) output from the particulate sensor 100 through the signal line 223. When a difference is produced between the reference potential of the secondary-side ground SGL and the reference potential of the primary-side ground PGL as a result of generation of the leakage current $I_{esc}$, the first operational amplifier AMP1 outputs a voltage corresponding to this difference. Since the voltage output from the first operational amplifier AMP1 correlates with the leakage current $I_{esc}$, this voltage is output to the sensor control section 600 through the wiring line 772 as a signal $SW_{esc}$ representing the leakage current $I_{esc}$.

Also, the voltage output from the first operational amplifier AMP1 produces the compensation current $I_c$, which is supplied from the wiring line LI2 to the wiring line 771 through the resistor RE2. As described above, the compensation current $I_c$ is equal to the leakage current $I_{esc}$. Therefore, as a result of supply of the compensation current $I_c$ to the wiring line 771 which constitutes the secondary-side circuit, the difference between the reference potential of the secondary-side ground SGL and the reference potential of the primary-side ground PGL is compensated.

The second operational amplifier AMP2 amplifies the signal $SW_{esc}$ input from the first operational amplifier AMP1, and outputs to the sensor control section 600 the signal $SS_{esc}$ obtained as a result of the amplification. Since the second operational amplifier AMP2 forms a differential amplification circuit, the second operational amplifier AMP2 outputs a voltage corresponding to the difference between the voltage input to one input terminal as the signal $SW_{esc}$ and the reference potential of the primary-side ground PGL input to the other input terminal. Namely, the second operational amplifier AMP2 outputs a voltage to the sensor control section 600 as the signal $SS_{esc}$, the voltage being obtained by amplifying the voltage of the input signal $SW_{esc}$ at a predetermined amplification factor (e.g., $10^3$ times).

The sensor control section 600 detects the amount of soot S contained in the exhaust gas through use of the signal $SW_{esc}$ (low sensitivity signal) and the signal $SS_{esc}$ (high sensitivity signal) input from the ion current measurement circuit 740. No particular limitation is imposed on the method of detecting the amount of soot S contained in the exhaust gas from these signals representing the leakage current $I_{esc}$. For example, in the case where the sensor control section 600 stores a map or a relational expression showing the relation between the voltage of the signal and the amount of soot S contained in the exhaust gas, the sensor control section 600 can calculate the amount of soot S contained in the exhaust gas by using the map or the relational expression.

The sensor control section 600 of the present embodiment obtains each of the voltages, which are analog signals input thereto as the signals $SS_{esc}$ and $SW_{esc}$, as a digital value of a predetermined resolution (for example, 8 bits). Also, the sensor control section 600 is configured such that the size of the voltage readable range (the range of the full scale) becomes the same for the signals $SS_{esc}$ and $SW_{esc}$ input thereto.

The signal $SS_{esc}$ (high sensitivity signal) has a higher sensitivity (resolution) for the leakage current $I_{esc}$ as compared with the signal $SW_{esc}$ (low sensitivity signal). For example, whereas a voltage level of the signal $SW_{esc}$ of 1 V corresponds to a magnitude of the leakage current $I_{esc}$ of 1 nA, a voltage level of the signal $SS_{esc}$ of 1 V corresponds to a magnitude of the leakage current $I_{esc}$ of 1 pA. Meanwhile, the sensor control section 600 has the same voltage resolution (the minimum recognizable potential difference) (for example, 0.02 V) for both the signals $SS_{esc}$ and $SW_{esc}$. Accordingly, the magnitude of the leakage current $I_{esc}$ corresponding to the voltage resolution of the sensor control section 600 is small for the case of the signal $SS_{esc}$ (e.g., 0.02 pA) and is large for the case of the signal $SW_{esc}$ (e.g., 0.02 nA). In other words, the sensor control section 600 can detect a smaller change in the leakage current $I_{esc}$ from signal $SS_{esc}$, as compared with the signal $SW_{esc}$.

Therefore, the amount of soot S contained in the exhaust gas obtained from the signal $SS_{esc}$ is smaller in the minimum recognizable unit and is higher in accuracy than the amount of soot S contained in the exhaust gas obtained from the signal $SW_{esc}$. Meanwhile, the readable voltage range (e.g., 0 to 5 V) of the sensor control section 600 is set to cover the entire voltage range of the signal $SW_{esc}$. Therefore, a range in which the amount of soot S contained in the exhaust gas can be measured through use of the signal $SW_{esc}$ is wider than a range in which the amount of soot S contained in the exhaust gas can be measured through use of the signal $SS_{esc}$. If the amount of soot S contained in the exhaust gas falls within a range corresponding to the entire voltage range of the signal $SW_{esc}$, the amount of soot S can be measured within the entire range.

As can be understood from the above, when the voltage of the signal $SS_{esc}$, falls within the readable voltage range, the sensor control section 600 can accurately measure the amount of soot S contained in the exhaust gas through use of the signal $SS_{esc}$, and when the voltage of the signal $SS_{esc}$, falls outside the readable voltage range, the sensor control section 600 can measure the amount of soot S contained in the exhaust gas through use of the signal $SW_{esc}$ which allows measurement within a wider range.

1-5. Corona Current Measurement Circuit

Figure 5:
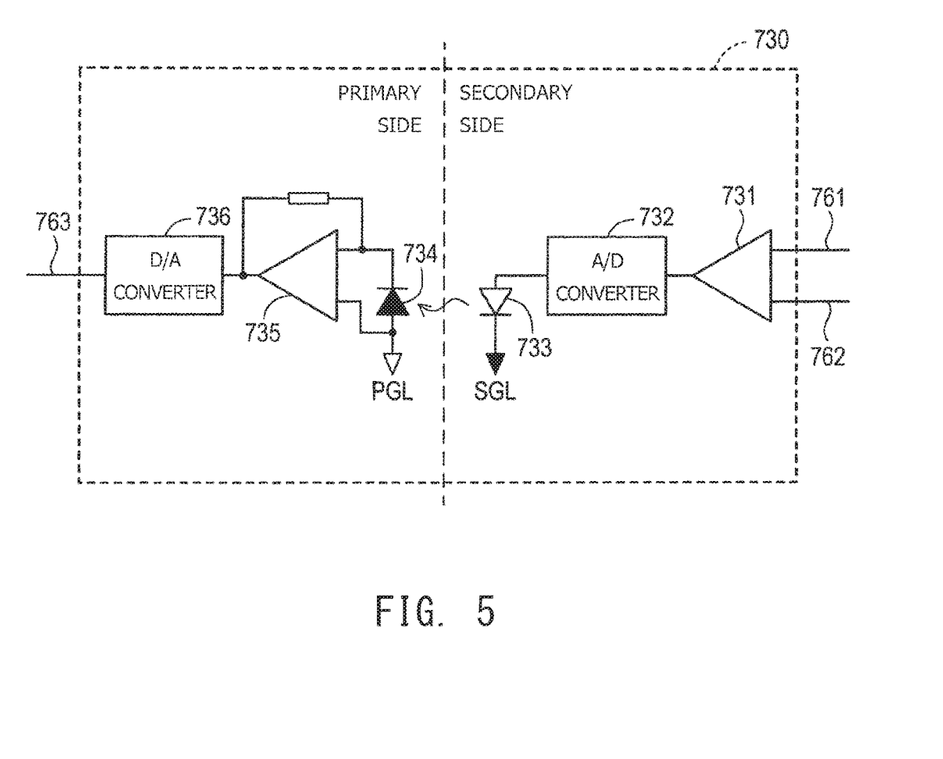
FIG. 5 is a circuit diagram schematically exemplifying the configuration of a corona current measurement circuit.

FIG. 5 is an explanatory view schematically exemplifying the configuration of the corona current measurement circuit 730. The corona current measurement circuit 730 is constituted as a so-called optical-coupling-type isolation amplifier whose input and output sides are isolated from each other. The input side of the corona current measurement circuit 730 belongs to the secondary side of the electric circuit section 700 (FIG. 3), and the output side of the corona current measurement circuit 730 belongs to the primary side of the electric circuit section 700. The corona current measurement circuit 730 includes a secondary-side operational amplifier 731, an A/D converter 732, a light emitting section 733, a light receiving section 734, a primary-side operational amplifier 735, and a D/A converter 736.

The two input terminals of the secondary-side operational amplifier 731 are connected to the wiring line 761 and the wiring line 762, respectively, and the output terminal thereof is connected to the A/D converter 732. The secondary-side operational amplifier 731 amplifies the potential difference between the wiring line 761 and the wiring line 762 and outputs the amplified potential difference to the A/D converter 732. The potential difference between the wiring line 761 and the wiring line 762 is the potential difference between the opposite ends of the shunt resistor 230 (FIG. 3) whose resistance is known, and correlates with the current flowing through the signal line 223 (FIG. 3) (the secondary-side current $(I_{dc}+I_{trp}+I_c)$). Namely, the secondary-side operational amplifier 731 amplifies an analogue voltage signal representing the magnitude of the current flowing through the signal line 223 (FIG. 3) and outputs the amplified analogue voltage signal to the A/D converter 732.

The A/D converter 732, which is connected to the secondary-side operational amplifier 731 and the light emitting section 733, converts the analog signal output from the secondary-side operational amplifier 731 to a digital signal and outputs the digital signal to the light emitting section 733.

The light emitting section 733 includes an LED and is connected to the A/D converter 732 and the secondary-side ground SGL. The light emitting section 733 converts the digital voltage signal output from the A/D converter 732 to an optical signal.

The light receiving section 734 includes a photodiode and is connected to the primary-side operational amplifier 735 and the primary-side ground PGL. The light receiving section 734 converts the optical signal output from the light emitting section 733 to a current signal and outputs the current signal to the primary-side operational amplifier 735. In this manner, the light emitting section 733 and the light receiving section 734 are electrically and physically isolated from each other, and signals are transmitted between the light emitting section 733 and the light receiving section 734 through the mediation of light.

The primary-side operational amplifier 735 is connected to the light receiving section 734 and the D/A converter 736, and forms a current-voltage-conversion circuit. The primary-side operational amplifier 735 convers the current signal output from the light receiving section 734 to a voltage signal and outputs the voltage signal to the D/A converter 736. The D/A converter 736, which is connected to the primary-side operational amplifier 735 and the wiring line 763, converts the digital signal output from the primary-side operational amplifier 735 to an analog signal and outputs the analog signal to the sensor control section 600 (FIG. 3) through the wiring line 763. Since the corona current measurement circuit 730 has the above-described configuration, the corona current measurement circuit 730 can output to the primary-side sensor control section 600 the signal input from the secondary-side signal line 223, while maintaining the isolation between the primary side and the secondary side.

1-6. Auxiliary Electrode Current Measurement Circuit

Figure 6:
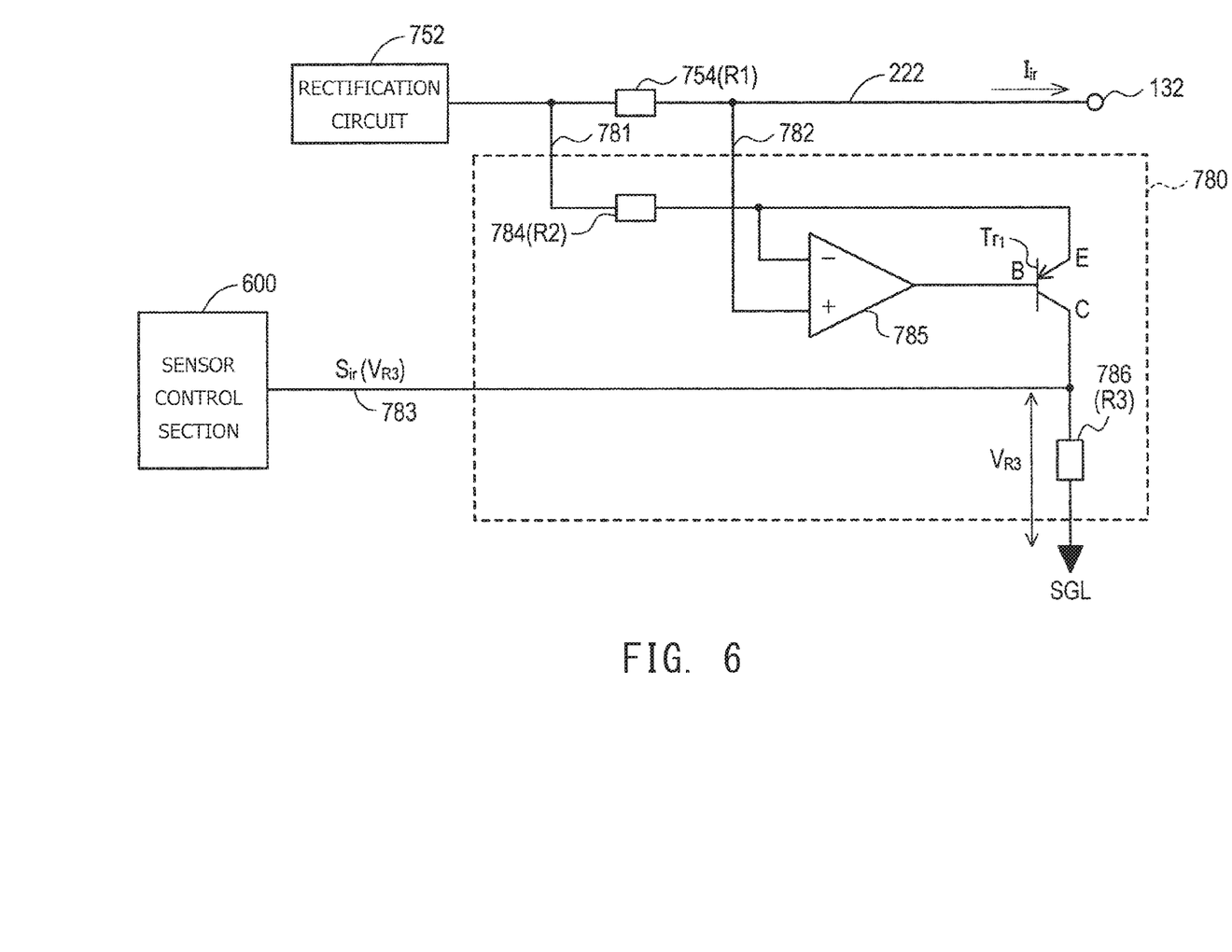
FIG. 6 is a circuit diagram schematically exemplifying the configuration of an auxiliary electrode current measurement circuit.

FIG. 6 is an explanatory view schematically exemplifying the configuration of the auxiliary electrode current measurement circuit 780. The auxiliary electrode current measurement circuit 780 includes a resistor 784, an operational amplifier 785, a transistor Tr1, and a resistor 786.

One input terminal of the operational amplifier 785 is connected to the second wiring line 222 at a position between the short protection resistor 754 and the second electrode 132. The other input terminal of the operational amplifier 785 is connected to the emitter of a transistor Tr1 and is connected, through the resistor 784, to the second wiring line 222 at a position between the short protection resistor 754 and the second rectification circuit 752. The output terminal of the operational amplifier 785 is connected to the base of the transistor Tr1. The transistor Tr1 is a PNP-type transistor, and its collector is connected to the secondary-side ground SGL through the resistor 786.

The connection point between the collector of the transistor Tr1 and the resistor 786 is connected to the sensor control section 600. Namely, the auxiliary electrode current measurement circuit 780 is configured to output to the sensor control section 600 an auxiliary electrode current signal $S_{ir}$ which represents the voltage $V_{R3}$ between the opposite ends of the resistor 786. Notably, since the voltage $V_{R3}$ between the opposite ends of the resistor 786 changes with the auxiliary electrode current $I_{ir}$, the auxiliary electrode current signal $S_{ir}$ can be utilized as a signal representing the auxiliary electrode current $I_{ir}$.

When the particulate sensor 100 is operating normally, although a voltage is applied from the second rectification circuit 752 to the second electrode 132 through the second wiring line 222, no current flows to the second wiring line 222 because the second electrode 132 and the casing CS are electrically insulated from each other. However, for example, in the case where soot or the like lowers the insulation resistance between the second electrode 132 and the casing CS to thereby form a short circuit therebetween, the auxiliary electrode current $I_{ir}$ flows between the second electrode 132 and the casing CS, and the auxiliary electrode current $I_{ir}$ flows to the second wiring line 222.

The magnitude of the auxiliary electrode current $I_{ir}$ can be calculated by expression (2) shown in [F2].

[F2]

$$I_{ir}=V_{R3}\times R2/\{(R1\times R3)\times(1-1/h_{FE})\} \qquad (2)$$

In expression (2), $V_{R3}$ is the voltage between the opposite ends of the resistor 786, $h_{FE}$ is the DC current amplification factor of the transistor Tr1, R1 is the resistance of the short protection resistor 754, R2 is the resistance of the resistor 784, and R3 is the resistance of the resistor 786. Of these values, the DC current amplification factor $h_{FE}$ is a known value determined by the characteristics of the operational amplifier 785, and the resistances R1, R2, and R3 are known values determined by the characteristics of the short protection resistor 754, resistor 784, and the resistor 786, respectively.

As described above, the sensor control section 600 can detect the voltage $V_{R3}$ between the opposite ends of the resistor 786 (hereinafter referred to as the "end-to-end voltage $V_{R3}$") based on the auxiliary electrode current signal $S_{ir}$ received from the auxiliary electrode current measurement circuit 780. Therefore, the sensor control section 600 can compute the magnitude of the auxiliary electrode current $I_{ir}$ through use of the end-to-end voltage $V_{R3}$ and the expression (2) by storing the expression (2) in advance.

1-7. Control of Corona Current

As described above, the sensor control section 600 controls the first discharge voltage control circuit 711a by using the signal $S_{dc+trp+c}$ supplied from the corona current measurement circuit 730 such that the input current $I_{in}$ becomes equal to the target current $I_{ta}$. Namely, the corona current measurement circuit 730 and the sensor control section 600 constitute a constant current circuit for maintaining the corona current (=the input current $I_{in}$) at a constant level.

For controlling the corona current (=the input current $I_{in}$), the sensor control section 600 uses an auxiliary electrode current signal $S_{ir}$ (auxiliary electrode current $I_{ir}$) in addition to the signal $S_{dc+trp+c}$ (secondary-side current ($I_{dc}+I_{trp}+I_c$)).

Specifically, the sensor control section 600 first calculates a corrected secondary-side current $I_{dc+trp+c}$ (=($I_{dc}+I_{trp}+I_c$)−$I_{ir}$), which is a value obtained by subtracting the auxiliary electrode current $I_{ir}$ from the secondary-side current ($I_{dc}+I_{trp}+I_c$). The sensor control section 600 then controls the amount of electric power supplied from the first isolation transformer 720a to the first electrode 112 of the particulate sensor 100 based on the result of comparison between the corrected secondary-side current $I_{dc+trp+c}$ and the target current $I_{ta}$ such that the corona current (=the input current $I_{in}$) approaches the target current $I_{ta}$.

For example, when the corrected secondary-side current $I_{dc+trp+trp+c}$ is larger than the target current $I_{ta}$, the sensor control section 600 controls the amount of electric power supplied to the first electrode 112 such that the corona current (=the input current $I_{in}$) decreases. In contrast, when the corrected secondary-side current $I_{dc+trp+c}$ is smaller than the target current $I_{ta}$, the sensor control section 600 controls the amount of electric power supplied to the first electrode 112 such that the corona current (=the input current $I_{in}$) increases.

If soot or the like lowers the insulation resistance between the second electrode 132 and the casing CS and the second electrode 132 and the casing CS are electrically shorted to each other, the auxiliary electrode current $I_{ir}$ may flow to the second wiring line 222. When such an auxiliary electrode current $I_{ir}$ flows to the secondary wiring line 222, due to the influence of the auxiliary electrode current $I_{ir}$, the detected value of the secondary-side current ($I_{dc}+I_{trp}+I_c$) varies. In the case where the amount of electric power is controlled through use of the detected value, the control of the amount of electric power by the sensor control section 600 is likely to deviate from a normal operating state. As a result, the amount of electric power supplied from the first isolation transformer 720a to the first electrode 112 may deviate from the normal operating state and the accuracy in measuring the amount of particulates may decrease.

In order to overcome such a drawback, the sensor control section 600 controls the amount of electric power supplied to the first electrode 112 by using the auxiliary electrode current $I_{ir}$ in addition to the secondary-side current ($I_{dc}+I_{trp}+I_c$). Thus, the sensor control section 600 can suppress the influence of the auxiliary electrode current $I_{ir}$ and prevent improper control of the amount of electric power supplied from the first isolation transformer 720a to the first electrode 112.

As a result, even when the auxiliary electrode current $I_{ir}$ flows, the sensor control section 600 can properly control the amount of electric power supplied from the first isolation transformer 720a to the first electrode 112, and can measure the amount of particulates while suppressing the influence of the auxiliary electrode current $I_{ir}$.

1-8. Effects

As described above, the particulate measurement system 10 of the present embodiment includes the auxiliary electrode current measurement circuit 780. Therefore, the particulate measurement system 10 can determine whether or not the auxiliary electrode current $I_{ir}$ has flowed to the secondary wiring line 222 and can detect the magnitude of the auxiliary electrode current $I_{ir}$.

When the particulate sensor 100 is operating normally, no current flows to the secondary wiring line 222 because the second electrode 132 and the casing CS are electrically insulated from each other. However, when the second electrode 132 and the casing CS are electrically shorted to each other by, for example, soot or the like, the auxiliary electrode current $I_{ir}$ may flow to the secondary wiring line 222. Namely, in the case where the auxiliary electrode current $I_{ir}$ is detected, there is a possibility that an anomaly of some kind has occurred in the particulate measurement system 10.

Therefore, the auxiliary electrode current measurement circuit 780 allows the particulate measurement system 10 to determine the state of adhesion of particulates, etc., in the particulate sensor 100 and determine whether or not the particulate measurement system 10 itself is anomalous. Thus, the particulate measurement system 10 can suppress a decrease in measurement accuracy due to adhesion of particulates.

Also, in the particulate measurement system 10, when the sensor control section 600 controls the corona current (=the input current $I_{in}$), the sensor control section 600 uses the auxiliary electrode current signal $S_{ir}$ (the auxiliary electrode current $I_{ir}$) in addition to the signal $S_{dc+trp+c}$ (the secondary-side current ($I_{dc}+I_{trp}+I_c$)). Specifically, the sensor control section 600 computes the corrected secondary-side current $I_{dc+trp+c}$ by subtracting the auxiliary electrode current $I_{ir}$ from the secondary-side current ($I_{dc}+I_{trp}+I_c$) and controls the amount of electric power supplied from the first isolation transformer 720a to the first electrode 112 based on the difference between the corrected secondary-side current $I_{dc+trp+c}$ and the target current $I_{ta}$.

Therefore, the sensor control section 600 can suppress the influence of the auxiliary electrode current $I_{ir}$ by controlling the amount of electric power supplied to the first electrode 112 through use of the auxiliary electrode current $I_{ir}$, and can prevent improper control of the amount of electric power supplied from the first isolation transformer 720a to the first electrode 112.

Accordingly, the particulate measurement system 10 can suppress a decrease in the particulate measurement accuracy even when adhesion of particulates or the like has occurred in the particulate sensor.

1-9. Corresponding Structure

In the above-described embodiment, the particulate measurement system 10 corresponds to the particulate measurement system of the invention; the particulate sensor 100 corresponds to the particulate sensor of the invention; the sensor drive section 300 corresponds to the sensor drive section of the invention; the ion generation section 110 corresponds to the ion generation section of the invention; the electrification chamber 121 corresponds to the electrification chamber of the invention; the ion trapping section 130 corresponds to the trapping section of the invention; and the second electrode 132 corresponds to the auxiliary electrode section of the invention.

The first isolation transformer 720a corresponds to the isolation transformer for corona discharge of the invention; the second isolation transformer 720b corresponds to the isolation transformer for auxiliary electrode of the invention; the primary-side ground PGL corresponds to the primary-side reference potential of the invention; and the secondary-side ground SGL corresponds to the secondary-side reference potential of the invention. The sensor control section 600 and the corona current measurement circuit 730 correspond to the corona discharge control section of the invention; and the secondary-side current ($I_{dc}+I_{trp}+I_c$) flowing to the signal line 223 corresponds to the current flowing from the trapping section to the secondary-side reference potential of the invention. The leakage current $I_{esc}$ corresponds to the leakage current of the invention. The sensor control section 600 and the auxiliary electrode current measurement circuit 780 correspond to the auxiliary electrode current detection section of the invention; and the secondary wiring line 222 corresponds to the voltage application path of the invention.

2. Other Embodiments

An embodiment of the present invention has been described; however, the present invention is not limited to the above-described embodiment and can be implemented in various forms without departing from the scope of the invention.

For example, in the above-described embodiment, the auxiliary electrode current $I_{ir}$ detected by the auxiliary electrode current measurement circuit 780 is used for controlling the corona current (control of the amount of electric power supplied from the first isolation transformer 720a to the first electrode 112). However, use of the auxiliary electrode current $I_{ir}$ is not limited thereto. For example, the embodiment may be modified to determine the state of adhesion of soot in the particulate sensor 100 based on the presence/absence of the auxiliary electrode current $I_{ir}$ to thereby determine the timing of cleaning or exchanging the particulate sensor 100. The particulate measurement accuracy can be improved by determining the timing of cleaning or exchanging the particulate sensor as described above.

The structure of the particulate measurement system is not limited to the structure in which the ion generation section is provided inside the particulate sensor, and the particulate measurement system may have a structure in which the ion generation section is provided separately from the particulate sensor. The corona current measurement circuit is not limited to the optical-coupling-type isolation amplifier and may be, for example, a magnetic-coupling-type or capacitive-coupling-type isolation amplifier.

In the above-described embodiment, the sensor control section 600 is configured to compute the corrected secondary-side current $I_{dc+trp+c}$ by subtracting the auxiliary electrode current $I_{ir}$ from the secondary-side current ($I_{dc}+I_{trp}+I_c$) and to control the amount of electric power supplied to the first electrode 112 based on the difference between the corrected secondary-side current $I_{dc+trp+c}$ and the target current $I_{ta}$. However, the configuration of the sensor control section is not limited thereto. For example, the sensor control section may be configured to compute a corrected target value $I_{ta}R$ which is the sum of the auxiliary electrode current $I_{ir}$ and the target current $I_{ta}$ and to control the amount of electric power supplied to the first electrode 112 based on the result of comparison between the secondary-side current ($I_{dc}+I_{trp}+I_c$) and the corrected target value $I_{ta}R$.

For example, when the secondary-side current ($I_{dc}+I_{trp}+I_c$) is greater than the corrected target value $I_{ta}R$, the sensor control section controls the amount of electric power supplied to the first electrode 112 such that the corona current (=the input current $I_{in}$) decreases. Meanwhile, when the secondary-side current ($I_{dc}+I_{trp}+I_c$) is smaller than the corrected target value $I_{ta}R$, the sensor control section controls the amount of electric power supplied to the first electrode 112 such that the corona current (=the input current $I_{in}$) increases.

As a result, even when the auxiliary electrode current $I_{ir}$ flows, the sensor control section can properly control the amount of electric power supplied from the first isolation transformer 720a to the first electrode 112, and can measure the amount of particulates while suppressing the influence of the auxiliary electrode current $I_{ir}$.

The particulate measurement system 10 of the above-described embodiment is configured to generate "positive ions" between the first electrode 112 and the partition wall 42 by means of corona discharge. However, the particulate measurement system 10 may configured to generate "negative ions" by means of corona discharge. For example, negative ions can be generated between the first electrode 112 and the partition wall 42 by changing the destinations of the positive and negative connections of the first electrode 112 and the partition wall 42. Also, in this case, when the polarity of ions generated by means of corona discharge is changed, the various sections of the particulate measurement system are properly adjusted, for example, by reversing the polarity of the voltage applied to the second electrode 132, whereby particulates (soot, etc.) can be measured properly.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2015-210885 filed Oct. 27, 2015, the above-noted application incorporated herein by reference in its entirety.

What is claimed is:

1. A particulate measurement system which comprises a particulate sensor for detecting particulates and a sensor drive section for driving the particulate sensor and which measures the amount of particulates contained in a gas under measurement, wherein the particulate sensor comprises:
an ion generation section for generating ions by means of corona discharge;
an electrification chamber for electrifying at least a portion of the particulates contained in the gas under measurement using the ions generated in the ion generation section;

a trapping section for trapping at least a portion of the ions generated by the ion generation section but not used for electrifying the particulates; and an auxiliary electrode section including an auxiliary electrode maintained at a potential which repulses the unused ions and which assists in the trapping of the unused ions at the trapping section, wherein the sensor drive section comprises:

an isolation transformer for corona discharge which has a primary-side coil and a secondary-side coil and which performs voltage conversion for electric power used for generating the corona discharge, the secondary-side coil of the isolation transformer for corona discharge being connected to the ion generation section, a reference potential of the primary-side coil of the isolation transformer for corona discharge being defined as a primary-side reference potential, and a reference potential of the secondary-side coil of the isolation transformer for corona discharge being defined as a secondary-side reference potential;

an isolation transformer for the auxiliary electrode which has a primary-side coil and a secondary-side coil and which performs voltage conversion for generating an auxiliary voltage to be applied to the auxiliary electrode, the secondary-side coil of the isolation transformer for the auxiliary electrode being connected to the auxiliary electrode section; and a corona discharge control section which detects current flowing from the trapping section to the secondary-side reference potential and which controls the amount of electric power supplied from the isolation transformer for corona discharge to the ion generation section based on the detected current such that the amount of ions generated by the ion generation section approaches a target value set in advance, wherein the sensor drive section further comprises an auxiliary electrode current detection section which detects auxiliary electrode current flowing to a voltage application path for connecting the secondary-side coil of the isolation transformer for the auxiliary electrode to the auxiliary electrode section.

2. The particulate measurement system as claimed in claim 1, wherein the corona discharge control section controls the amount of electric power supplied from the isolation transformer for corona discharge to the ion generation section based on the auxiliary electrode current, in addition to the current flowing from the trapping section to the secondary-side reference potential, such that the amount of ions generated from the ion generation section approaches the target value set in advance.

* * * * *